(12) United States Patent
Stumpf

(10) Patent No.: US 6,926,746 B2
(45) Date of Patent: Aug. 9, 2005

(54) PROTECTION OF REDUCTION-SENSITIVE DYES

(75) Inventor: Martin Stumpf, Grenzach-Wyhlen (DE)

(73) Assignee: Clariant Finance (BVI) Limited, Tortola (VG)

( * ) Notice: Subject to any disclaimer, the term of this patent is extended or adjusted under 35 U.S.C. 154(b) by 175 days.

(21) Appl. No.: 10/467,695

(22) PCT Filed: Feb. 11, 2002

(86) PCT No.: PCT/IB02/00406

§ 371 (c)(1), (2), (4) Date: Aug. 8, 2003

(87) PCT Pub. No.: WO02/064881

PCT Pub. Date: Aug. 22, 2002

(65) Prior Publication Data

US 2004/0074017 A1 Apr. 22, 2004

(30) Foreign Application Priority Data

Feb. 13, 2001 (CH) .............................................. 0248/01

(51) Int. Cl.$^7$ .............................. D06P 1/607; D06P 1/66
(52) U.S. Cl. ........................ 8/576; 8/594; 8/598; 8/606
(58) Field of Search ........................... 8/543, 576, 650, 8/653, 598, 606, 490

(56) References Cited

U.S. PATENT DOCUMENTS

| | | | | |
|---|---|---|---|---|
| 5,085,668 A | * | 2/1992 | Pelster et al. .................... | 8/549 |
| 5,142,020 A | | 8/1992 | Kud et al. ................... | 528/272 |
| 6,153,723 A | | 11/2000 | Lang et al. .................. | 528/300 |

FOREIGN PATENT DOCUMENTS

| | | |
|---|---|---|
| DE | 27 30 313 | 1/1979 |
| DE | 31 02 315 | 1/1982 |
| EP | 0 442 101 | 8/1991 |
| EP | 0 964 015 | 12/1999 |
| FR | 70732 | * 7/1959 |
| GB | 2 003 937 | 3/1979 |
| WO | WO 01/56385 | 8/2001 |

OTHER PUBLICATIONS

English abstract for DE 3102315, Jan. 14, 1982.
XP–002199899, "Beilsteins Handbuch Der Organischen Cheimie", Vierte Auglage, 2. Erganzungs–werk, Neunter Band, 1949, Freidrich Richter, Springer Verlag, p. 263.

* cited by examiner

*Primary Examiner*—Margaret Einsmann
(74) *Attorney, Agent, or Firm*—Anthony A. Bisulca

(57) ABSTRACT

The invention relates to a process for protecting reduction-sensitive dyes in the course of dyeing or printing fiber materials with dyes using a compound of the formula (I) or a mixture thereof

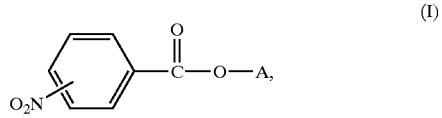

(I)

where the substituents are each as defined in the claims; novel compounds of the formula (I) and printing and dyeing media containing compounds of the formula (I).

6 Claims, No Drawings

PROTECTION OF REDUCTION-SENSITIVE DYES

The present invention relates to a process for protection of reduction-sensitive dyes in the course of dyeing or printing fiber materials by addition of reduction protectants, novel reduction protectants and dyeing or printing media containing these reduction protectants.

Reduction phenomena occur very frequently in dyeings on cellulose fiber material, since regenerated cellulose fibers especially occasionally contain residues of reducing substances from their production process which lead to these undesirable effects.

Similarly, dyeing processes involving high temperatures, for example pad steam, lead to a yield loss in the case of reduction-sensitive dyes. The associated effects show up in a reduced color yield especially. In the case of light-colored hues, this negative effect is particularly serious.

The dyes to be protected by the process of the invention against reductive effects on cellulose substrates are in particular vat dyes, direct dyes and reactive dyes. Among reactive dyes they are in particular those which are azo, anthraquiinone or phthalocyanine based and which contain at least one known reactive substituent such as for example a β-hydroxyethyl sulphone sulphuric ester, vinylsulphonyl, 2,2,3,3-tetra-fluorocyclobutane-1-acryloylamino, monochlorotriazine, monofluorotriazine, dichlorotriazine, difluorotriazine, vinylsulphonylamino, β-hydroxyethylsulphonylaminosulphuric ester and β-phenylsulphonylpropionylamino group.

Protectable dyes having at least two reactive groups to attach the dye which bears nucleophilic groups to the fiber as a bridge member include for example 1,3,4-tris-(acryloyl) hexahydro-s-triazine, methylenebisacrylamide or 2,4,6-triethyleneimino-s-triazine.

Useful dyes which react with the fiber via these bifunctional compounds preferably include those dyes of the azo and anthraquinone series where the nucleophilic groups include for example sulphonamide, N-monosubstituted sulphonamide, hydroxyl, mercapto and/or acetoacetyl groups and/or heterocyclic ring systems containing imino groups.

The reactive dyes described above may be fixed by adding the requisite amounts of alkali, for example sodium bicarbonate, anhydrous sodium carbonate or alkaline donor, to the printing ink or liquor and in the case of a continuous process steaming the principle dyeings in saturated or superheated steam or exposing them to the action of dry heat. In the case of an exhaust process, the dyeing liquor containing the substrate is heated.

However, it is also possible to prepare the dye batches without addition of alkali and to fix the dyes in a two step process whereby the alkali is applied to the textile material in a second step, for example by pad-mangling, nip-padding or dipping and the material may subsequently be subjected to a short steaming process or to a prolonged batching process without heating.

The inventive method of efficient reduction prevention includes other dyeing classes as well, especially direct and vat dyes.

It is known that undesirable reduction of dyes in dyeing or printing can be controlled with alkali metal salts of m-nitrobenzenesulphonic acid. But the efficacy of these compounds frequently leaves something to be desired. Moreover, the low water solubility of these substances leads to dyeing problems. The salts of m-nitrobenzenesulphonic acid are therefore usually added in solid form, which can lead to dusting. This is not without its dangers owing to the toxicity of the compounds and is therefore ideally to be avoided.

The reduction protectants customarily used in dyeing and printing, such as chlorate and chromate, are unsuitable, since chlorate is ineffective in an alkaline medium and chromate leads to dulling of the hue.

It is an object of the present invention to provide a process for protection of reduction-sensitive dyes which avoids the disadvantages of the hitherto customary processes.

This object is achieved by a process for protecting reduction-sensitive dyes in the course of dyeing or printing fiber materials with dyes, characterized in that the dyeing or print process utilizes a compound of the formula (I) or a mixture thereof

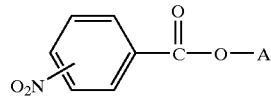

(I)

where

A is a suitable counter-cation, or

A is

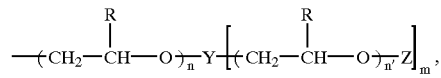

where

R is hydrogen or linear or branched $C_{1-4}$alkyl,

Y is hydrogen, a direct bond,

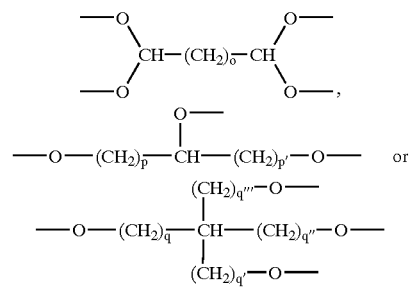

where o, p, p', q, q', q" and q''' are independently 1, 2 or 3,

Z is hydrogen or

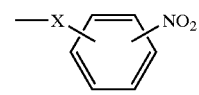

where X is a direct bond or a $C_{1-4}$alkylene group, n and n' are each a natural number subject to the proviso that n and n' are independent of each other and n is never 0, m is 0 when Y is hydrogen, is 1 when Y is a direct bond, is 2 when Y is

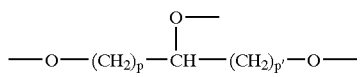

or
is 3 when Y is

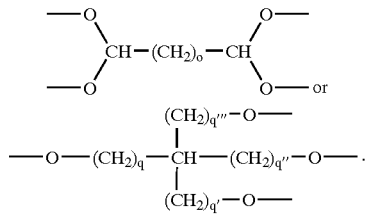

The counterion A may be any customary cation which has no effect on the dyeing. Especially alkali metal ions or quaternary nitrogen compounds, for example $^+N(C_{1-4}alkyl)_4$, $^+NH(C_{1-4}alkyl)_3$, $^+NH_2(C_{1-4}alkyl)_2$, $^+NH_3(C_{1-4}alkyl)$. The alkyl groups may be linear or branched. The alkyl groups may additionally be substituted. Useful substituents include in particular —OH, —NH$_2$, —CN, halogens or $C_{1-4}$alkoxy groups. Preferred counterions are in particular $^+NH(C_{2-4}alkyl-OH)_3$.

Preferred processes are characterized in that a compound of the formula (I) or a mixture thereof where
A is

n is from 1 to 10, n' is from 0 to 10 and
Y is hydrogen, a direct bond,

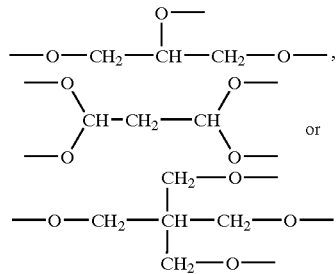

are used.

Further more preferred processes are characterized by the use of compounds of formula (I) or mixtures thereof where the —NO$_2$ group is attached to the phenylring at position 4 or 3.

Further more preferred processes are characterized in that A is $^+N(C_{1-4}alkyl)_4$, $^+NH(C_{1-4}alkyl)_3$, $^+NH_2(C_{1-4}alkyl)_2$ or $^+NH_3(C_{1-4}alkyl)$, wherein the alkyl group may be unsubstituted or substituted.

More preferred processes are characterized in that A is $^+N(C_{2-4}alkyl)_4$, $^+NH(C_{2-4}alkyl)_3$, $^+NH_2(C_{2-4}alkyl)_2$ or $^+NH_3(C_{2-4}alkyl)$, wherein the alkyl group may be unsubstituted or substituted by —OH, —NH$_2$, —CN, halogen or $C_{1-4}$alkoxy and where the —NO$_2$ group is attached to the phenylring at position 4 or 3.

Further more preferred processes are characterized by use of compounds of the formula (I) where n is from 1 to 5, n' is from 0 to 5 and Y is a direct bond.

The present invention also provides compounds of the formula (Ia)

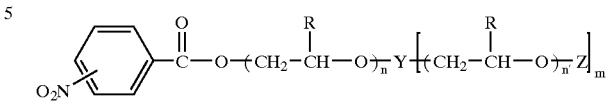

(Ia)

where the substituents are each as defined above.
In preferred compounds
R is H or $C_{1-2}$alkyl,
Y is hydrogen when m is 0 or a direct a bond when m is 1,
Z is hydrogen,
n is from 1 to 10,
n' is from 0 to 10 and
m is 0 or 1.

The present invention also provides dyeing and printing media containing the above-mentioned reduction protectants. The level of reduction protectants is preferably 0.05–10% by weight based on the total weight of the liquor.

When the reduction protectants are present in the form of a print paste, the fraction of the reduction protectant in the paste can be arbitrarily varied.

Print pastes are prepared using customary thickeners. Such thickeners include for example neutral, weakly alkaline or weakly acidic alginates, gums, alkylcelluloses or hydroxyethercelluloses and also mixtures thereof and emulsions or semiemulsions prepared therefrom by means of suitable emulsifiers.

The compounds of the formula (I) where A is a suitable counterion are prepared according to the generally known syntheses described in the literature.

The compounds of the formula (Ia) are prepared catalytically in EP 964015 and EP 442101. The preferred catalyst is p-toluenesulphonic acid monohydrate. Further catalysts are described in EP 442101. The condensation reaction is preferably carried out at temperatures of 80° C.–190° C. The reaction can be carried out under atmospheric pressure or under reduced pressure.

The examples which follow illustrate the invention. Percentages are by weight, unless otherwise stated, and degrees are in Celsius.

PREPARATION EXAMPLE 1

83.55 parts of 4-nitrobenzoic acid, 240 parts of polyethylene glycol having an average molecular weight of 400D and 1 part of p-toluoenesulphonic acid monohydrate are initially charged to a sulphonation flask and heated to 120° C. under reduced pressure while the water of reaction is distilled off. The internal temperature of the reaction mixture is raised to 190° C. in the course of 2 hours. Stirring is then continued at 190° C. for 2 hours under a pressure of 45 mbar. The compound thus obtained is cooled to room temperature under atmospheric pressure and diluted with 20.9 parts of an oleic acid polyglycol ester (7EO) and 20.9 parts of butyl polyglycol for better emulsifiability.

PREPARATION EXAMPLE 2

Preparation Example 1 is repeated except that 4-nitrobenzoic acid is replaced by 3-nitrobenzoic acid. The compound thus obtained is likewise cooled to room temperature under atmospheric pressure and diluted with 20.9 parts of an oleic acid polyglycol ester (7EO) and 20.9 parts of butyl polyglycol for better emulsifiability.

PREPARATION EXAMPLE 3

167.1 parts of 4-nitrobenzoic acid and 173.7 parts of demineralized water are heated to 80° C. with stirring. 159.2 parts of triethanolamine are added at pH 7.2 at 80° C. in the course of one hour. The mixture is subsequently stirred at 80° C. for 30 minutes until a clear solution has formed.

PREPARATION EXAMPLE 4

Preparation Example 3 is repeated except that 4-nitrobenzoic acid is replaced by 3-nitrobenzoic acid.

USE EXAMPLES

Use Example A 1800 parts of an aqueous liquor containing 2 parts of the product of Preparation Example 1 and 140 parts of sodium chloride are entered with 100 parts of woven cotton fabric. The bath is admixed with a solution of 3.3 parts of Reactive Blue 52 in 100 parts of water and the liquor is heated to 98° C. After 30 minutes 10 parts of 3% sodium hydroxide solution are added, followed at intervals of 5 minutes by a further four times 10 parts of 3% sodium hydroxide solution, after which dyeing is continued at 90° C. for a further 40 minutes. This is followed by cooling and the dyeing is finished in a conventional manner by soaping, rinsing and drying. This affords a very level, clean and reproducible blue dyeing in a high yield.

Use Example A'

A comparative dyeing without addition of product of Preparation Example 1 shows an approximately 5% less deep shade and a hue shift into green.

Use Example B

Use Example A is repeated except that C.I. Reactive Blue 52 is replaced by the same amount of Reactive Yellow 165. This affords a perfectly level and reproducible yellow dyeing in high cleanness.

Use Example B'

A comparative dyeing without addition of the product of Preparation Example 1 shows an approximately 5% less deep shade and lower brilliance.

Use Example C 100 parts of a woven cotton fabric have applied to them 80 parts of a liquor containing 33 g/l of Reactive Blue 52. The fabric is dried at 140° C. for 1 minute and then has applied to it 80 g of a liquor containing per liter 10 g of the product of Preparation Example 3, 250 g of sodium chloride, 20 g of sodium carbonate and 10 g of 30% sodium hydroxide solution. The fabric thus treated is treated with saturated steam at 104° C. for 4 minutes. This is followed by cooling and the dyeing is finished in a conventional manner by soaping, rinsing and drying. This affords a very level, clean and reproducible blue dyeing in a high yield.

Use Example C'

A comparative dyeing without addition of product of Preparation Example 3 shows an approximately 10% less deep shade and a hue shift into green.

Use Example D

Use Example A is repeated except that C.I. Reactive Blue 52 is replaced by the same amount of Reactive Yellow 165. This affords a perfectly level and reproducible yellow dyeing in high cleanness and yield.

Use Example D'

A comparative dyeing without addition of the product of Preparation Example 3 shows reduced brilliance.

What is claimed is:
1. Process for protecting reduction-sensitive dyes in the course of dyeing or printing fiber materials with dyes, where a dyeing or a print process utilizes a compound of the formula (I) as well as mixtures thereof

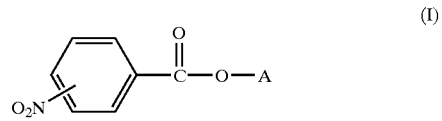

where
A is a quaternary ammonium ion, or
A is

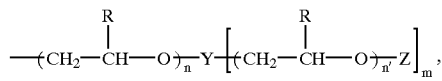

where
R is hydrogen or linear or branched $C_{1-4}$ alkyl group,
Y is hydrogen, a direct bond,

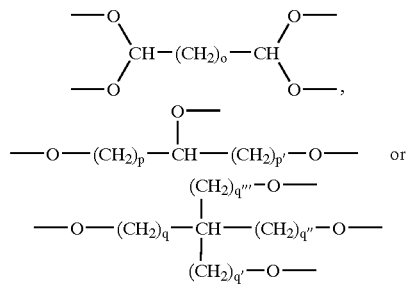

where o, p, p', q, q', q" and q''' are independently 1, 2 or 3,
Z is hydrogen or

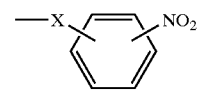

where X is a direct bond or a $C_{1-4}$alkylene group,
n and n' are each a natural number subject to the proviso that n and n' are independent of each other and n is never 0,
m is 0 when Y is hydrogen, is 1 when Y is a direct bond, is 2 when Y is

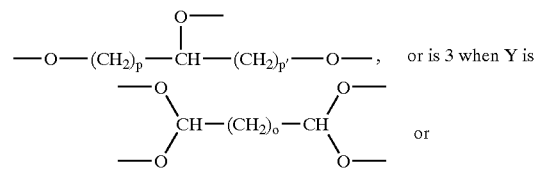

or is 3 when Y is

-continued

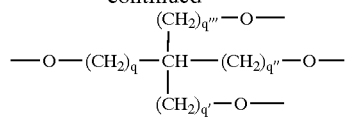

2. Process according to claim 1, where said compound of formula (I) or a mixture thereof where the —NO$_2$ group is attached to the phenylring at position 4 or 3 are used.

3. Process according to claim 1, where A is $^+$N(C$_{1-4}$alkyl)$_4$, $^+$NH(C$_{1-4}$alkyl)$_3$, $^+$NH$_2$(C$_{1-4}$alkyl)$_2$ or $^+$NH$_3$(C$_{1-4}$alkyl), wherein the alkyl group may be unsubstituted or substituted.

4. Process according to claim 1, where said compound of the formula (I) or a mixture thereof where A is a group of the formula

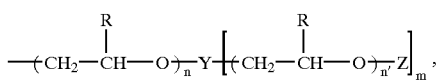

n is from 1 to 10,
n' is from 0 to 10 and
Y is hydrogen, a direct bond.

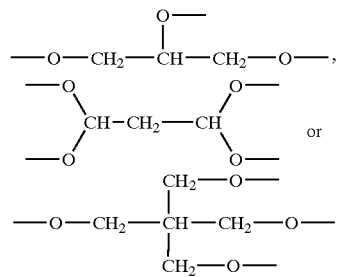

are used.

5. Process according claim 1, where said compound of the formula (I) or a mixture thereof
where
n is from 1 to 5, n' is from 0 to 5,
Y is hydrogen or a direct bond, and
m is 0 or 1
are used.

6. Process according to claim 1, where said dyes are reactive dyes, direct dyes or vat dyes.

\* \* \* \* \*